US010349911B2

(12) United States Patent
Melchionna et al.

(10) Patent No.: US 10,349,911 B2
(45) Date of Patent: Jul. 16, 2019

(54) SYSTEM AND METHOD TO PRODUCE CORRECTED CONTRAST LEVELS IN A CT SCAN OF VASCULATURE

(71) Applicant: Dassault Systemes Simulia Corp., Johnston, RI (US)

(72) Inventors: Simone Melchionna, Belmont, MA (US); Brian Fix, Waltham, MA (US)

(73) Assignee: Dassault Systemes Simulia Corp., Johnston, RI (US)

(*) Notice: Subject to any disclaimer, the term of this patent is extended or adjusted under 35 U.S.C. 154(b) by 0 days.

(21) Appl. No.: 15/598,476

(22) Filed: May 18, 2017

(65) Prior Publication Data
US 2018/0333125 A1  Nov. 22, 2018

(51) Int. Cl.
| A61B 6/00 | (2006.01) |
| G06F 19/00 | (2018.01) |
| G06T 5/00 | (2006.01) |
| G16H 50/50 | (2018.01) |
| A61B 90/00 | (2016.01) |

(52) U.S. Cl.
CPC .......... *A61B 6/5258* (2013.01); *A61B 6/481* (2013.01); *A61B 6/504* (2013.01); *A61B 6/5217* (2013.01); *G06F 19/321* (2013.01); *G06T 5/009* (2013.01); *G16H 50/50* (2018.01); *A61B 2090/3762* (2016.02); *G06T 2207/10081* (2013.01); *G06T 2207/30101* (2013.01)

(58) Field of Classification Search
None
See application file for complete search history.

(56) References Cited

U.S. PATENT DOCUMENTS

2016/0342765 A1* 11/2016 Sankaran ............. A61B 5/7275

OTHER PUBLICATIONS

Eslami et al., "Computational Study of Computed Tomography Contrast Gradients in Models of Stenosed Coronary Arteries." Journal of Biomechanical Engineering, Sep. 2015, vol. 137. pp. 1-34.*

* cited by examiner

*Primary Examiner* — James M Kish
(74) *Attorney, Agent, or Firm* — Fish & Richardson P.C.

(57) ABSTRACT

A method, system, and computer program product for correcting the contrast levels of a medical image of a vascular system is described. One of the methods includes identifying a global reference contrast level. The method includes for each image location which represents a location within the vascular system, determining a corrected contrast level by multiplying the original contrast level of that location by the ratio of the global reference contrast level divided by a local reference contrast level.

16 Claims, 4 Drawing Sheets

SYSTEM AND METHOD TO PRODUCE CORRECTED CONTRAST LEVELS IN A CT SCAN OF VASCULATURE

BACKGROUND

A Computed Tomography (CT) scan makes use of combinations of X-ray images taken from different angles to produce cross-sectional images of specific areas of a scanned object.

CT scans are used in a variety of different medical applications, including analysis of the head, the lungs, the pulmonary system, heart, and abdominal areas. CT scans can be used, for example, to detect stenosis in the vascular system.

SUMMARY

This specification describes technologies relating to medical image processing.

A method, computer program product, and system for correcting the contrast levels of a medical image of a vascular system is described herein.

In general, one aspect of the subject matter described in this specification can be embodied in methods that include the act of identifying a global reference contrast level. The methods include the act of for each image location which represents a location within the vascular system, determining a corrected contrast level by multiplying the original contrast level of that location by the ratio of the global reference contrast level divided by a local reference contrast level. The methods also include the act of producing a medical image in which contrast at each image location is adjusted using the corrected contrast Other embodiments of this aspect include corresponding computer systems, apparatus, and computer programs recorded on one or more computer storage devices, each configured to perform the actions of the methods. A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

The foregoing and other embodiments can each optionally include one or more of the following features, alone or in combination. The global reference contrast level may be determined from a reference location that represents a location within the aorta ostium. The methods may include the act of generating a representation of vascular system based on the image locations with corrected contrast levels. The methods may include the act of generating a fluid flow simulation based on the representation of the vascular system. The methods may include the act of generating a physical model based on the representation of the vascular system. The methods may include the act of presenting the representation of the vascular system to a doctor. The methods may include the acts of identifying a starting region of the vascular system as a reference point for the global contrast level, identifying distal extremities of the vascular system, identifying the set of paths within the vascular system, each path in the set of paths connecting the starting region to one of the distal extremities, identifying a centerline for each path, and for each image location which represents a location within the vascular system, using the contrast level of the nearest centerline location as the local reference contrast level.

The details of one or more embodiments of the subject matter described in this specification are set forth in the accompanying drawings and the description below. Other features, aspects, and advantages of the subject matter will become apparent from the description, the drawings, and the claims.

DETAILED DESCRIPTION

Figure 1:
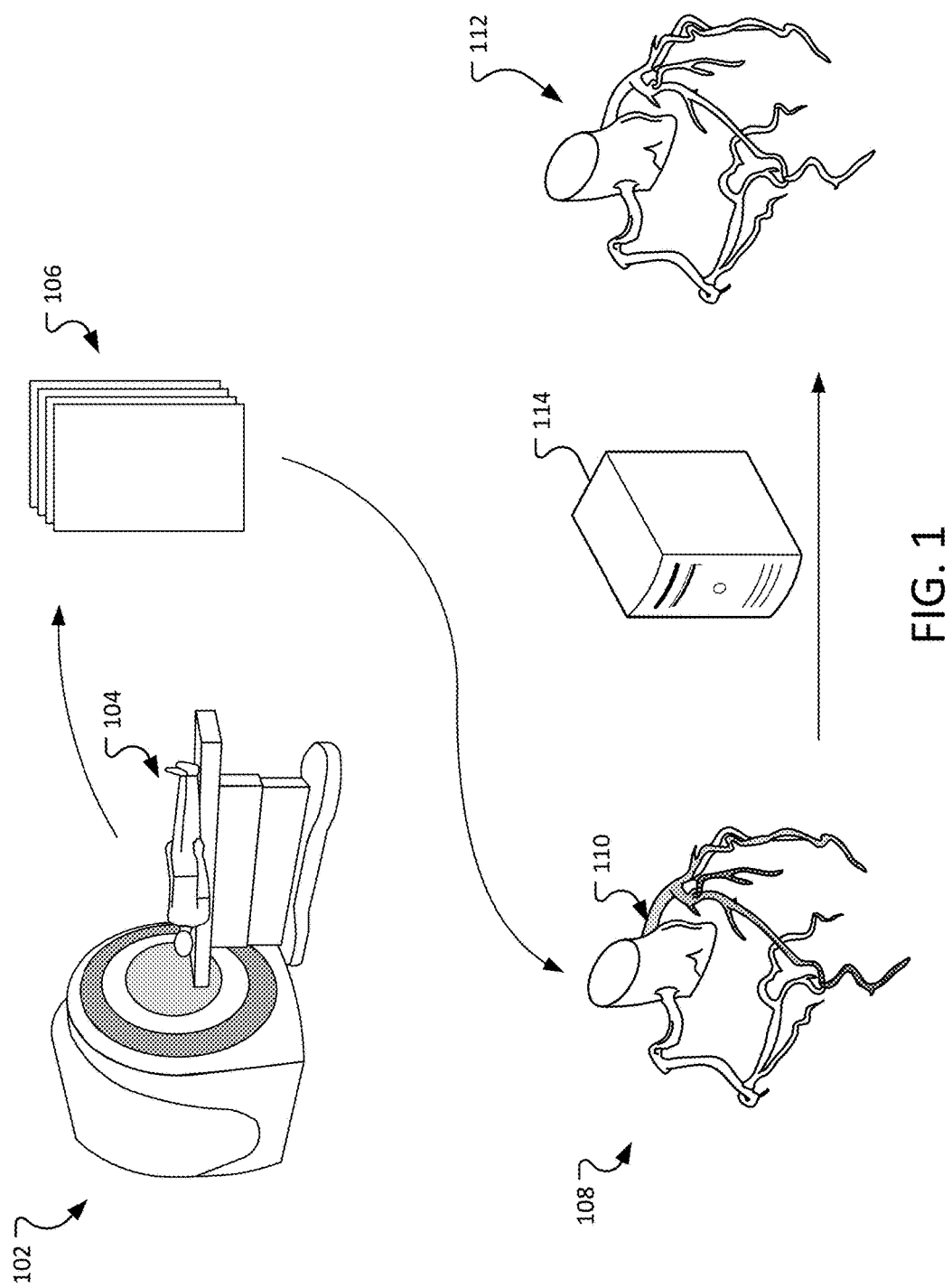
FIG. 1 is diagram illustrating a three dimensional image of an area of interest using CT scans.

FIG. 1 is diagram illustrating a three dimensional image of an area of interest using CT scans. Computed tomography (CT) is a computerized imaging procedure in which a narrow beam of x-rays is aimed at a patient and quickly rotated around the body, producing signals that are processed by the machine's computer to generate cross-sectional images. A CT scanner 102 uses a motorized x-ray source that rotates around a patient 104. Each time the x-ray source completes one full rotation, the CT computer constructs a 2D image slice 106 of the patient. The system can take multiple image slices 106 of the patient.

Image slices can be used to generate a 3D image 108 of an area of interest of the patient 104. In this example, the area of interest is a portion 110 of the coronary arteries system. However, the 3D image generated using the 2D image slices is not perfect. The medical process coupled with the x-ray technology used in the CT scan introduces artifacts that distort the 3D image. These artifacts result in inaccuracies in the representation of the coronary arteries system.

A computer system 114 can adjust the 3D image to remove and/or compensate for these inaccuracies and thereby produce a more accurate 3D representation 112 of the coronary arteries.

Figure 2:
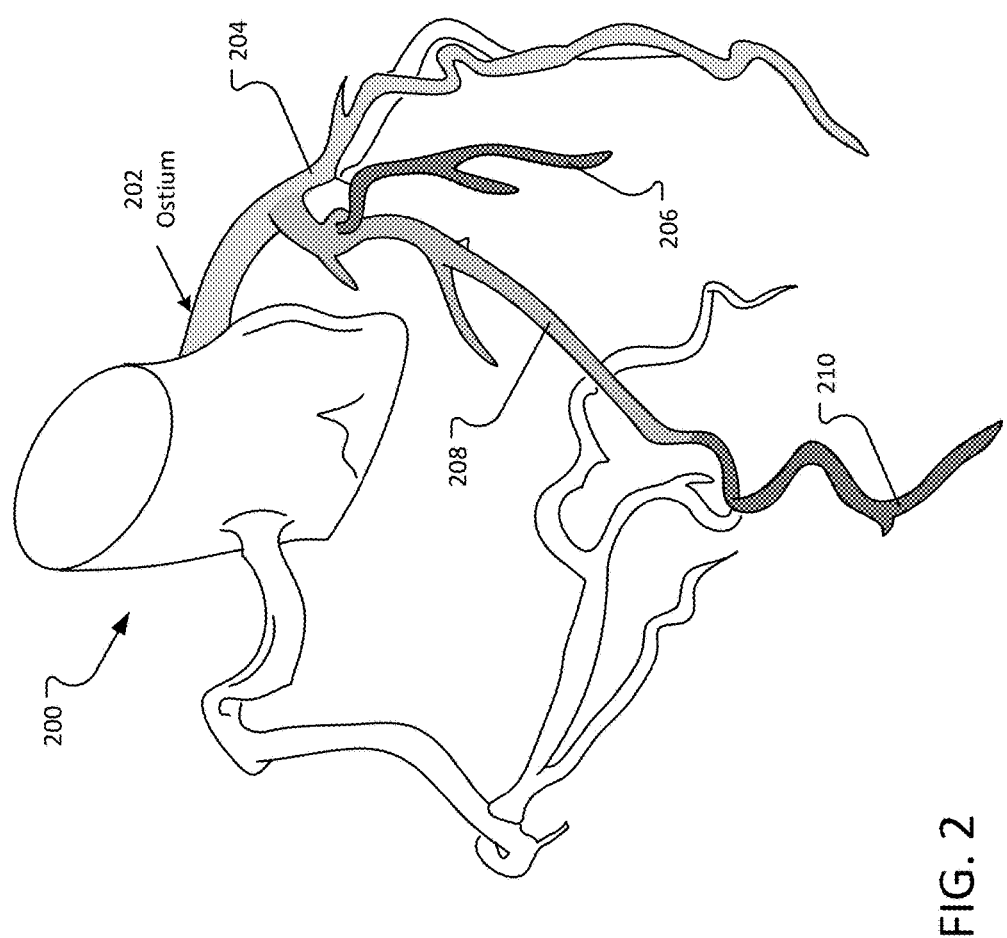
FIG. 2 illustrates a pre-corrected representation of a part of the coronary arteries system.

FIG. 2 illustrates a pre-corrected representation of a part of the coronary arteries system 200. A CT image of the coronary arteries is typically acquired by injecting an iodinated contrast liquid to enhance the vessels signal from the background. The contrast is injected in a transient fashion and consequently does not uniformly fill the coronary trees, in particular contrast is typically higher in the aortic region (ostium 202) and lower in the peripheral region. In addition, the phenomenon presents non-linearities and strong modulations in the neighborhood of stenoses (abnormal narrowing of a passage in the body). These observations are broadly referred to as Transluminal Attenuation Gradient (TAG). The non-linearities and modulations can make it more difficult to identify stenosis because it is difficult to tell if the difference in contrast is caused by a non-uniformity of the contrast fluid or because of a stenosis.

In this example, the coronary arteries system 200 illustrates an example of TAG, different areas (for example, area 204, 206, 208, and 210) have a different based level of contrast. The different base level of contrast can cause stenosis to appear more severe or may introduce other inaccuracies. While the illustration shows areas as having uniform contrast within a particular area, such consistency is not necessary and is used here for purposes of illustration. Instead, the contrast level may continually vary throughout the 3D image.

TAG depends on multiple physiological and anatomical factors that cannot be predicted in advance. Radiologists take into account the possible and frequent bias introduced by TAG when they interpret the vascular morphology, but only via a visual, experience-based approach. This experience is unique to the individual radiologist and has not previously been replicable in using software or procedural algorithmic techniques.

As such, there is need to be more accurate than visual inspection allows for interpreting the coronary lumen morphology correctly, for both quantitative evaluation, diagnostic assessment of coronary disease and/or for simulating the blood flow in reconstructions of the coronary vessels.

One problem resulting from TAG is that TAG induces tapering effects which cause a lumen to appear smaller in the distal regions. When a threshold-based segmentation is applied to a vessel having TAG, the resulting cross-sectional areas of the vessels are smaller than the actual cross sectional area of the vessels in the patient. This effect related to the distance of the location from the aorta and introduces artifacts into the vessel shape. It is desirable to correct for TAG such that the visual assessment of the vascular lumen is more accurate due to a reduction in artifacts, the quantitative evaluation of the vascular lumen is close to reality, and a segmentation method based on a single universal threshold value can be used reliably to segment the entire coronary tree.

A computer system can navigate through the coronary tree, probe the local contrast level, correct for the local attenuations and/or modulation, and restore the contrast level based on a reference level, typically taken in the aorta. The resulting corrected image exhibits characteristics of a more ideal filling of the entire coronary tree by the contrast agent. This in turn allows a threshold-based image segmentation process to generate an accurately reconstructed geometry of the region of interest.

A further advantage of the system described below is that the process is rapid and cost effective. As such, it does not overly tax the computational resources of the computer system and can be performed in near real time.

Figure 3:
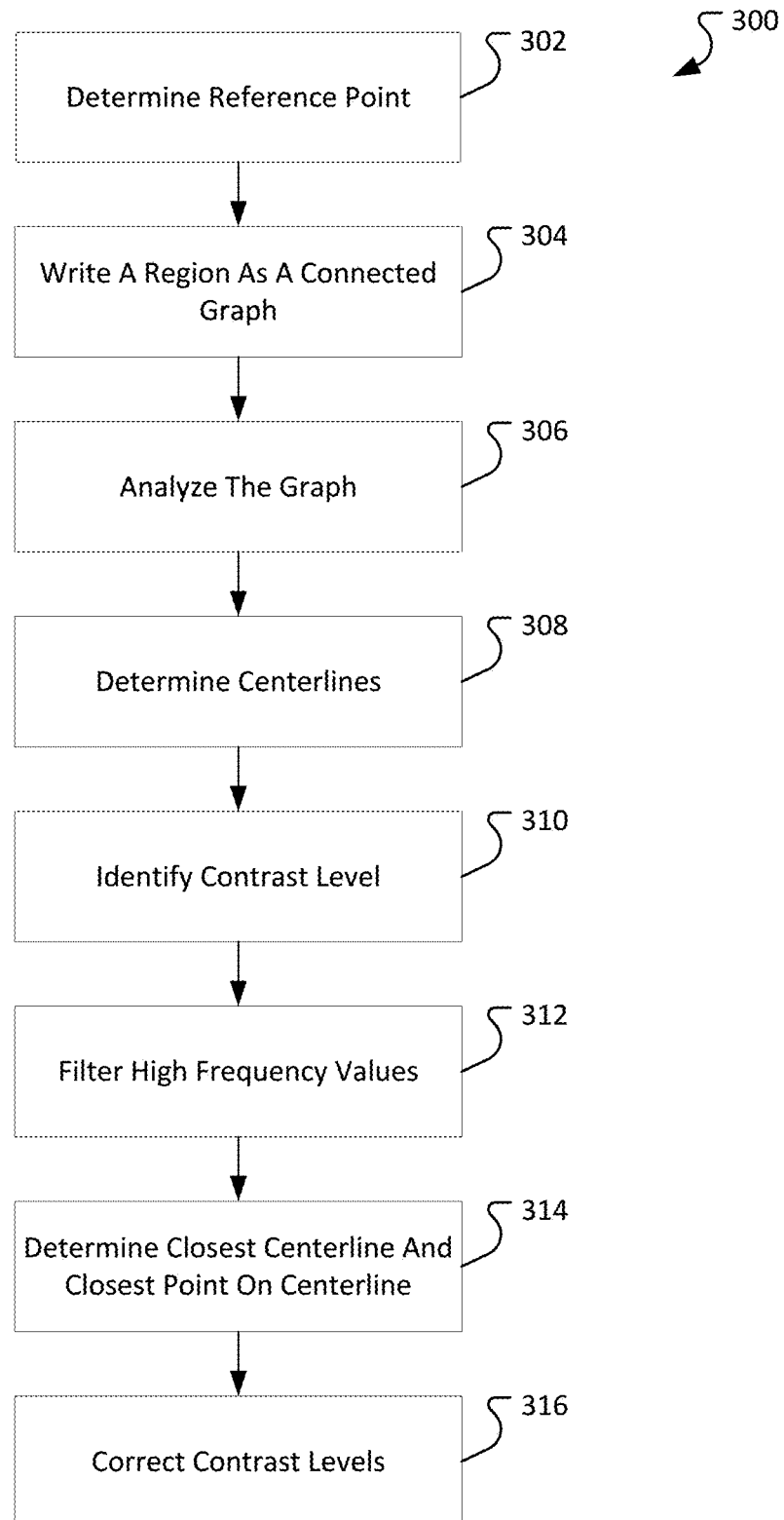
FIG. 3 is a flowchart of an example of a process to correct the effects of TAG on a CT scan.
Figure 4:
FIG. 4 illustrates an example of the process described in FIG. 3 as applied to representation of a part of the coronary arteries system Like reference numbers and designations in the various drawings indicate like elements.

FIG. 3 is a flowchart of an example of a process 300 to correct the effects of TAG on a CT scan. The process can be performed by a computer system analyzing a CT scan. The process 300 will be described in reference to FIG. 4. FIG. 4 illustrates an example of the process 300 applied to representation of a part of the coronary arteries system 400.

The process 300 determines 302 a reference point in the aorta ostium (for example, the reference point 402 of FIG. 4). In some implementations, the reference point can be determined manually by placing a marker on the 3D image. In some implementations, the reference point can be determined automatically by recognizing the aorta. For example, the aorta may be identified using a filter that tracks and identifies the regular, circular section of the aorta.

The process 300 identifies 302 a region of interest (in this example, the region of interest is a region of the coronary system), which contains the aorta and associated vascular structure (for example, the region of interest 400 of FIG. 4). Identifying the region of interest can be performed by sculpting, semi-automatic or automatic conventional methods. In some implementations, the region of interest may be provided to the system as part of an initial setup.

The process 300 rewrites 304 the region of interest as a connected graph. The graph may be generated based on the CT image slices or the initial 3D image, where each pixel is a node in the graph and neighboring pixels are connected by a leaf.

The process 300 analyzes 306 the graph, find the distal extremities. The process can set a market for each identified distal extremity.

The process 300 determines 308 centerlines from the ostium to the markers. For example, the process may execute a best-path algorithm from ostium to each marker (for example, using the Dijkstra method). The best path may be considered the centerline for the path (for example, the centerline 404 of FIG. 4).

The process 300 identifies 310 a contrast level for each node/pixel on the centerlines.

The process 300 filters-out 312 high-frequency values of contrast level. For example, the process may use a linear convolution (an operation that calculates the output for a linear spatial invariant given as input and the corresponding response) or a low pass filter (a filter that passes signals with a frequency lower than a certain cutoff frequency and attenuates signals with frequencies higher than the cutoff frequency). In some implementations, the process may use other filtering and/or spatial smoothing techniques to filter high frequency values.

The process 300 determines 314, for all pixels in the 3D image, among all possible centerlines, the closest point on a centerline to the corresponding pixel. For example, referring to FIG. 4, for pixel/node 406, the process may identify the point 408 on the centerline 404 as the closest point.

The process 300 corrects 316 the contrast level for each pixel by multiplying its original contrast level by the ratio of the ostium contrast level divided by the contrast level of the closest centerline point. For example, referring to FIG. 4, to correct the contrast level for the pixel/node 406 the system can multiple the contrast at the pixel/node 406 by the ratio of the contrast at the reference point 402 and the contrast at the closest point 408 on the centerline 404.

Contrast inhomogeneity spontaneously occurs in coronary CT and is particularly strong in presence of stenoses. The local adjustment described above enables using a single, universal threshold to determine the vascular tree, without prior knowledge of the vessel wall or local morphology.

This approach further reverts the conventional notion that a local threshold should be used for vessel segmentation, or other but more involved approaches should be used to determine the lumen (watershed, region growing, gradient detection, . . . ).

The system is insensitive to the details of the lumen, the degree of arterial branching, the presence of multiple and nontrivial calcifications or stenoses of different severity, making it a generally applicable method.

It can be also applied to other types of CT or MM-based imaging modalities, as long as a contrast liquid is utilized, or by using a contrast agent that obeys the same type of principle: local injection and image acquisition during the transient and before the contrast fills the whole territory uniformly.

EXAMPLE APPLICATIONS

The process described above thus recalibrates (i.e., clarifies) the 3D image(s) produced from the 2D slices to provide new or updated 3D image(s). The new or updated 3D image(s) form a 3D representation of the region of interest. Applications of the process include diagnosis of stenosis or other cardio vascular issues, geometrical reconstruction of the coronary system, and/or reproducing blood flow patterns by simulation. The system for correcting the contrast levels of a medical image of a vascular system, includes processor device(s) and hardware storage device(s) storing instructions that are operable to identify a reference contrast level and for each image location within the vascular system, determine a corrected contrast level by multiplying its original contrast level by the ratio of the global reference contrast level divided by a local reference contrast level and produce new or updated 3D image(s) with corrected contrast 316. The operations performed by the processor include generating a representation of the vascular system based on the image locations with corrected contrast levels and/or generating a fluid flow simulation 319 based on the representation of the vascular system. The system can also execute operations that generate a physical model 320 based on the representation of the vascular system, using otherwise conventional physical model generation approaches.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs (i.e., one or more modules of computer program instructions, encoded on computer storage mediums for execution by, or to control the operation of, data processing apparatus). A computer storage medium can be, or be included in, a computer-readable storage device, a computer-readable storage substrate, a random or serial access memory array or device, or a combination of one or more of them. The computer storage medium can also be, or be included in, one or more separate physical components or media (e.g., multiple CDs, disks, or other storage devices). The computer storage medium can be non-transitory.

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example, a programmable processor, a computer, a system on a chip, or multiple ones, or combinations, of the foregoing. The apparatus can include special purpose logic circuitry (e.g., an FPGA (field programmable gate array) or an ASIC (application-specific integrated circuit)). The apparatus can also include, in addition to hardware, code that creates an execution environment for the computer program in question (e.g., code that constitutes processor firmware, a protocol stack, a database management system, an operating system, a cross-platform runtime environment, a virtual machine, or a combination of one or more of them). The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural or object-oriented or functional languages, and it can be deployed in any form, including as a stand-alone program or as a module, component, subroutine, service, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry (e.g., an FPGA (field programmable gate array) or an ASIC (application-specific integrated circuit)).

Processors suitable for the execution of a computer program include, by way of example, both general and special purpose microprocessors, and any one or more processors of any kind of digital, analog or quantum computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive, data from or transfer data to, or both, one or more mass storage devices for storing data (e.g., electronic, magnetic, magneto-optical disks, or optical disks), however, a computer need not have such devices. Moreover, a computer can be embedded in another device (e.g., a mobile telephone, a personal digital assistant (PDA), a mobile audio or video player, a game console, a GPS receiver, or a portable storage device (e.g., a universal serial bus (USB) flash drive)), to name just a few. Devices suitable for storing computer program instructions and data include all forms of non-volatile memory, media and memory devices, including by way of example semiconductor memory devices (e.g., EPROM, EEPROM, and flash memory devices), magnetic disks (e.g., internal hard disks or removable disks), magneto-optical disks, and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback) and input from the user can be received in any form, including acoustic, speech, or tactile input. In addition, a computer can interact with a user by sending documents to and receiving documents from a device that is used by the user (for example, by sending web pages to a web browser on a user's user device in response to requests received from the web browser).

Embodiments of the subject matter described in this specification can be implemented in a computing system that includes a back-end component (e.g., as a data server), a middleware component (e.g., an application server), or a front-end component (e.g., a user computer having a graphical user interface or a Web browser through which a user can interact with an implementation of the subject matter described in this specification), or any combination of one or more such back-end, middleware, or front-end components. The components of the system can be interconnected by any form or medium of digital or optical data communication (e.g., a communication network). Examples of communication networks include a local area network ("LAN") and a wide area network ("WAN"), an inter-network (e.g., the Internet), and peer-to-peer networks (e.g., ad hoc peer-to-peer networks).

The computing system can include users and servers. A user and server are generally remote from each other and typically interact through a communication network. The relationship of user and server arises by virtue of computer programs running on the respective computers and having a user-server relationship to each other. In some embodiments, a server transmits data (e.g., an HTML page) to a user device (e.g., for purposes of displaying data to and receiving user input from a user interacting with the user device). Data generated at the user device (e.g., a result of the user interaction) can be received from the user device at the server.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can, in some cases, be excised from the combination, and the claimed combination may be directed to a sub combination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A system for correcting the contrast levels of an image produced by a CT scan of a vascular system, the system comprising:
   one or more processing devices and one or more hardware storage devices storing instructions that are operable, when executed by the one or more processing devices, to cause the one or more processing devices to:
   identify a reference contrast level within the image;
   generate a graph structure from at least a portion of interest in the image, with pixels at least a portion of interest in the image represented as nodes of the graph structure;
   calculate plural local reference contrast levels;
   iteratively determine for at least some of the nodes, a corrected contrast level, by instructions to:
   multiply the original contrast level of a given one of the at least some nodes by the ratio of the reference contrast level divided by a local reference contrast level that is the closest local reference contrast level to the given node; and
   produce a corrected image from the nodes in the graph including the at least some nodes.

2. The system of claim 1, wherein the reference contrast level is determined from a reference location that represents a location within the aorta ostium.

3. The system of claim 1, wherein the instructions further comprise instructions to:
   display the corrected image on a monitor.

4. The system of claim 3, wherein the instructions further comprise instructions to:
   generate a fluid flow simulation based on the corrected image of the vascular system.

5. The system of claim 3, wherein the instructions further comprise instructions to:
   generate a physical model based on the representation of the vascular system.

6. The system of claim 1, wherein the instructions further comprise instructions to:
   identify in the graph, nodes corresponding to distal extremities of the vascular system; and
   set a marker for each node representing a corresponding distal extremity in the graph.

7. The system of claim 6, further comprising instructions to:
   identifying a node that is a starting region of the vascular system as a reference point for the contrast level;
   identifying a set of paths within the vascular system, each path in the set of paths connecting the node in the starting region to one of the identified nodes that correspond to distal extremities;
   identifying a centerline for each path to provide the calculated plural local reference contrast levels.

8. A computer-implemented method for correcting the contrast levels of an image produced by a CT scan of a vascular system, the method comprising:
   identifying a reference contrast level within the image;
   generating a graph structure from at least a portion of interest in the image where pixels in the at least a portion of interest in the image are represented as nodes of the graph structure;
   calculating plural local reference contrast levels;
   iteratively determining for at least some of the nodes, a corrected contrast level by multiplying the original contrast level of a given one of the at least some nodes by the ratio of the reference contrast level divided by a local reference contrast level that is the closet local reference contrast level to the given node; and producing a corrected image from the nodes in the graph including the at least some nodes.

9. The computer-implemented method of claim 8, wherein the reference contrast level is determined from a reference location that represents a location within the aorta ostium.

10. The computer implemented method of claim 8, further comprising generating displaying the corrected image on a monitor.

11. The computer implemented method of claim 10, further comprising generating a fluid flow simulation based on the corrected image.

12. The computer-implemented method of claim 10, further comprising generating a physical model based on the representation of the vascular system.

13. The computer-implemented method of claim 8, further comprising:
 identifying in the graph, nodes corresponding to distal extremities of the vascular system; and
 setting a marker for each node representing a corresponding distal extremity in the graph.

14. The computer-implemented method of claim 13, further comprising:
 identifying a node that is a starting region of the vascular system as a reference point for the contrast level;
 identifying a set of paths within the vascular system, each path in the set of paths connecting the node in the starting region to one of the identified nodes that correspond to distal extremities;
 identifying a centerline for each path to provide the calculated plural local reference contrast levels.

15. A computer program product tangibly stored on a computer readable medium, the computer program product for correcting contrast levels of an image produced by a CT scan of a vascular system, the computer program product comprising instructions to cause a computer system to:
 identify a node that is a reference contrast level within the image;
  generating a graph structure from at least a portion of interest in the image where pixels in the at least a portion of interest in the image are represented as nodes of the graph structure;
 calculate plural local reference contrast levels; and
 iteratively determine for at least some of the nodes, a corrected contrast level, by instructions to:
 multiply the original contrast level of a given one of the at least some nodes by the ratio of the reference contrast level divided by a local reference contrast level that is the closest local reference contrast level to the given node; and
 produce a corrected image from the nodes in the graph including the at least some nodes.

16. The computer program product of claim 15, further comprising instructions to:
 identify a node that is a starting region of the vascular system as a reference point for the contrast level;
 identifying a node that corresponds to a distal extremity of the vascular system;
 identifying a path within the vascular system, the path connecting the identified node in the starting region to the identified node that corresponds to a distal extremity;
 identifying a centerline for the path to provide the calculated plural local reference contrast levels.

* * * * *

UNITED STATES PATENT AND TRADEMARK OFFICE
CERTIFICATE OF CORRECTION

PATENT NO. : 10,349,911 B2  
APPLICATION NO. : 15/598476  
DATED : July 16, 2019  
INVENTOR(S) : Simone Melchionna and Brian Fix Page 1 of 1

It is certified that error appears in the above-identified patent and that said Letters Patent is hereby corrected as shown below:

In the Claims

Column 9, Claim 10, Line 1, delete "computer implemented" and insert --computer-implemented--.

Column 9, Claim 11, Line 1, delete "computer implemented" and insert --computer-implemented--.

Signed and Sealed this  
Eighth Day of October, 2019

Andrei Iancu  
*Director of the United States Patent and Trademark Office*